(12) United States Patent
Cunha Neto et al.

(10) Patent No.: US 8,338,582 B2
(45) Date of Patent: Dec. 25, 2012

(54) ANTI-HIV IMMUNOGENS AND METHODS FOR INDUCING AN IMMUNE RESPONSE

(75) Inventors: Edecio Cunha Neto, São Paulo (BR); Jorge Elias Kalil Filho, São Paulo (BR); Simone Goncalves Da Fonseca, São Paulo (BR)

(73) Assignees: Fundacao de Amparo a Pesquisa do Estado de Sao Paulo, Sao Paulo (BR); Fundacao Zerbini, Sao Paulo (BR); Universidade de Sao Paulo-USP, Sao Paulo (BR)

( * ) Notice: Subject to any disclaimer, the term of this patent is extended or adjusted under 35 U.S.C. 154(b) by 369 days.

(21) Appl. No.: 12/073,401

(22) Filed: Mar. 5, 2008

(65) Prior Publication Data

US 2008/0260766 A1   Oct. 23, 2008

Related U.S. Application Data

(63) Continuation-in-part of application No. PCT/BR2006/000175, filed on Sep. 4, 2006.

(30) Foreign Application Priority Data

Sep. 5, 2005 (BR) ..................................... 0504117

(51) Int. Cl.
*C07H 21/04* (2006.01)
*A61K 39/21* (2006.01)
(52) U.S. Cl. .................... 536/23.7; 424/208.1
(58) Field of Classification Search .................. None
See application file for complete search history.

(56) References Cited

U.S. PATENT DOCUMENTS

| 6,413,517 B1 | 7/2002 | Sette et al. |
| 2005/0137387 A1 * | 6/2005 | Mullins et al. ............. 536/23.72 |

FOREIGN PATENT DOCUMENTS

| WO | 0170772 A2 | | 9/2001 |
| WO | WO 03/046176 | * | 6/2003 |
| WO | WO 2004/084939 | * | 10/2004 |

OTHER PUBLICATIONS

Matthews et al., 1987, AIDS Research and Human Retroviruses, 3(1):197-206.*
Burton and Moore, Nature Medicine Vaccines Supplement, 1998, 4(5):495-498.*
Desrosiers, Nature Medicine, 2004, 10(3):221-223.*
Ayyavoo et al., AIDS, 2000, 14:1-9.*
Makitalo et al., Journal of General Virology, 2004, 85, 2407-2419.*
Lieberman J, Fabry JA, Fong DM, Parkerson GR 3rd. "Recognition of a small number of diverse epitopes dominates the cytotoxic T lymphocytes response to HIV type 1 in an infected individual." AIDS Res Hum Retroviruses. Mar. 20, 1997;13(5):383-92.

* cited by examiner

*Primary Examiner* — Zachariah Lucas
*Assistant Examiner* — Nicole Kinsey White
(74) *Attorney, Agent, or Firm* — Sughrue Mion, PLLC

(57) ABSTRACT

The present invention refers to new epitopes recognized by CD4+ T-lymphocytes. In addition, the present invention refers to the uses of such epitopes and their combinations, particularly in the treatment or prevention of disorders caused by the HIV-1 virus.

The present invention also refers to a composition comprising said epitopes and the uses of said composition, particularly in the treatment or prevention of disorders caused by the HIV-1 virus.

The present invention also refers to anti-HIV-1 prophylactic vaccines and therapeutic vaccines.

Furthermore, the present invention refers to a method for the identification of epitopes and methods for treating or preventing an infection caused by the HIV-1 virus.

14 Claims, 6 Drawing Sheets

FIG. 1

[p17 (73-88)] [p24 (33-45)] [p24 (131-150)] [p6 (32-46)] [pol (63-77)] [pol (136-150)] [pol (335-350)] [gp160 (19-28)] [gp160 (19-31)]

[gp160 (174-185)] [gp160 (196-205)] [gp160 (421-435)] [rev (11-27)] [vif (66-75)] [vpr (65-82)] [vpu (155-186)] [tat (45-58)] [nef (125-194)]

▨ Novel epitopes

<u>AAG CTT</u> <u>ACC ATG</u> GAG GAG CTG AGA AGC CTG TAC AAC ACC GTG GCC
ACC CTG TAC TGC GTG CAC GGC CCC GGC CCC GGC AGC CCC GAG GTG
ATC CCC ATG TTC AGC GCC CTG AGC GAG GGC CCC GGC CCC GGC AAG
AGA TGG ATC ATC CTG GGC CTG AAC AAG ATC GTG AGA ATG TAC AGC
CCC ACC AGC ATC GGC CCC GGC CCC GGC GAC AAG GAG CTG TAC CCC
CTG GCC AGC CTG AGA AGC CTG TTC GGC GGC CCC GGC CCC GGC CAG
AGA CCC CTG GTG ACC ATC AAG ATC GGC GGC CAG CTG AAG GAG GGC
CCC GGC CCC GGC ACC CCC GTG AAC ATC ATC GGC AGA AAC CTG CTG
ACC CAG ATC GGC GGC CCC GGC CCC GGC GGC AAG ATC ATC CTG GTG
GCC GTG CAC GTG GCC AGC GGC TAC ATC GGC CCC GGC CCC GGC AGA
GAC CTG CTG CTG ATC GTG ACC AGA ATC GTG GAG CTG CTG GGC AGA
GGC CCC GGC CCC GGC ACC ATG CTG CTG GGC ATG CTG ATG ATC TGC
AGC GCC GCC GGC CCC GGC CCC GGC GCC CTG TTC TAC AAG CTG GAC
GTG GTG CCC ATC GAC GGC CCC GGC CCC GGC AAC ACC AGC TAC AGA
CTG ATC AGC TGC AAC ACC AGC GTG ATC GGC CCC GGC CCC GGC AGC
GAG CTG TAC CTG TAC AAG GTG GTG AAG ATC GAG CCC CTG GGC GTG
GCC CCC GGC CCC GGC CCC GGC GAG CTG CTG AAG ACC GTG AGA CTG
ATC AAG TTC CTG TAC CAG AGC AAC CCC GGC CCC GGC CCC GGC GAG
GCC ATC ATC AGA ATC CTG CAG CAG CTG CTG TTC ATC CAC TTC GGC
CCC GGC CCC GGC CAG CAG CTG CTG TTC ATC CAC TTC AGA ATC GGC
TGC AGA CAC AGC AGA ATC GGC GGC CCC GGC CCC GGC AGC CTG CAG
TAC CTG GCC CTG GTG GCC CTG GTG GCC CCC AAG AAG GGC CCC GGC
CCC GGC GTG CTG GCC ATC GTG GCC CTG GTG GTG GCC ACC ATC ATC
GCC ATC GGC CCC GGC CCC GGC GTG CTG GAG TGG AGA TTC GAC AGC
AGA CTG GCC TTC CAC CAC GTG <u>TAG</u> <u>CTC GAG</u>

AAG CTT — Hind III site
ACC ATG — Kozak sequence
TAG — Stop codon
CTC GAG — Xho I site
GGC CCC CGC CCC GGC — spacers multiepitope gene:
pVAX-HIVBr18

```
                         SEQUENCE LISTING

<160> NUMBER OF SEQ ID NOS: 16

<210> SEQ ID NO 1
<211> LENGTH: 17
<212> TYPE: PRT
<213> ORGANISM: Artificial Sequence
<220> FEATURE:
<223> OTHER INFORMATION: HIV-1-derived peptide

<400> SEQUENCE: 1

Glu Glu Leu Arg Ser Leu Tyr Asn Thr Val Ala Thr Leu Tyr Cys Val His
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: HIV-1-derived peptide

<400> SEQUENCE: 2

Ser Pro Glu Val Ile Pro Met Phe Ser Ala Leu Ser Glu
1               5                   10

<210> SEQ ID NO 3
<211> LENGTH: 20
<212> TYPE: PRT
<213> ORGANISM: Artificial Sequence
<220> FEATURE:
<223> OTHER INFORMATION: HIV-1-derived peptide

<400> SEQUENCE: 3

Lys Arg Trp Ile Ile Leu Gly Leu Asn Lys Ile Val Arg Met Tyr Ser Pro Thr
1               5                   10                  15

Ser Ile
    20

<210> SEQ ID NO 4
<211> LENGTH: 15
<212> TYPE: PRT
<213> ORGANISM: Artificial Sequence
<220> FEATURE:
<223> OTHER INFORMATION: HIV-1-derived peptide

<400> SEQUENCE: 4

Asp Lys Glu Leu Tyr Pro Leu Ala Ser Leu Arg Ser Leu Phe Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: HIV-1-derived peptide

<400> SEQUENCE: 5

Gln Arg Pro Leu Val Thr Ile Lys Ile Gly Gly Gln Leu Lys Glu
1               5                   10                  15

<210> SEQ ID NO 6
```

-continued

```
<211> LENGTH: 15
<212> TYPE: PRT
<213> ORGANISM: Artificial Sequence
<220> FEATURE:
<223> OTHER INFORMATION: HIV-1-derived peptide

<400> SEQUENCE: 6

Gly Lys Ile Ile Leu Val Ala Val His Val Ala Ser Gly Tyr Ile
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: HIV-1-derived peptide

<400> SEQUENCE: 7

Thr Met Leu Leu Gly Met Leu Met Ile Cys Ser Ala Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: HIV-1-derived peptide

<400> SEQUENCE: 8

Ala Leu Phe Tyr Lys Leu Asp Val Val Pro Ile Asp
1               5                   10

<210> SEQ ID NO 9
<211> LENGTH: 14
<212> TYPE: PRT
<213> ORGANISM: Artificial Sequence
<220> FEATURE:
<223> OTHER INFORMATION: HIV-1-derived peptide

<400> SEQUENCE: 9

Asn Thr Ser Tyr Arg Leu Ile Ser Cys Asn Thr Ser Val Ile
1               5                   10

<210> SEQ ID NO 10
<211> LENGTH: 18
<212> TYPE: PRT
<213> ORGANISM: Artificial Sequence
<220> FEATURE:
<223> OTHER INFORMATION: HIV-1-derived peptide

<400> SEQUENCE: 10

Ser Glu Leu Tyr Leu Tyr Lys Val Val Lys Ile Glu Pro Leu Gly Val Ala Pro
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: HIV-1-derived peptide

<400> SEQUENCE: 11

Glu Leu Leu Lys Thr Val Arg Leu Ile Lys Phe Leu Tyr Gln Ser Asn Pro
1               5                   10                  15

<210> SEQ ID NO 12
<211> LENGTH: 15
<212> TYPE: PRT
```

```
<213> ORGANISM: Artificial Sequence
<220> FEATURE:
<223> OTHER INFORMATION: HIV-1-derived peptide

<400> SEQUENCE: 12

Glu Ala Ile Ile Arg Ile Leu Gln Gln Leu Leu Phe Ile His Phe
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: HIV-1-derived peptide

<400> SEQUENCE: 13

Gln Gln Leu Leu Phe Ile His Phe Arg Ile Gly Cys Arg His Ser Arg Ile Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: HIV-1-derived peptide

<400> SEQUENCE: 14

Ser Leu Gln Tyr Leu Ala Leu Val Ala Leu Val Ala Pro Lys Lys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: HIV-1-derived peptide

<400> SEQUENCE: 15

Val Leu Glu Trp Arg Phe Asp Ser Arg Leu Ala Phe His His Val
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: HIV-1-derived peptide

<400> SEQUENCE: 16

Val Leu Ala Ile Val Ala Leu Val Val Ala Thr Ile Ile Ala Ile
1               5                   10                  15
```

ANTI-HIV IMMUNOGENS AND METHODS FOR INDUCING AN IMMUNE RESPONSE

This application is a Continuation-In-Part, under 35 U.S.C. §111(a) and 37 C.F.R. §1.53, of International Application PCT/BR2006/000175, filed Sep. 4, 2006, in accordance with the procedures outlined in sections 1895 et Seq. of the Manual of Patent Examining Procedure. Priority is claimed from Brazilian Application No. PI 0504117-1 filed Sep. 5, 2005.

FIELD OF THE INVENTION

The present invention refers to one or more epitopes recognized by CD4+ T-lymphocytes, as well as the use of said epitopes and their combinations, particularly in the treatment or prevention of disorders caused by the HIV-1 virus.

The present invention also refers to a composition comprising said epitopes and to an use of said composition.

In addition, the present invention refers to anti-HIV-1 prophylactic and therapeutic vaccines.

Furthermore, the present invention refers to a method for the identification of epitopes and methods for treating or preventing infections caused by the HIV-1 virus.

BACKGROUND OF THE INVENTION

Although the development of an effective vaccine against HIV-1 is urgent, in view of the 40 million people currently infected with the virus, no effective vaccine for this purpose has been developed yet.

In 2003, at least 18 experimental prophylactic vaccines were known to be undergoing clinical trials (Phases 1 to 3) (McMichael A J & Hanke T, *Nature Medicine,* 2003) and an even greater number of pre-clinical approaches attempting the preparation of an effective vaccine. Almost all of the products well known in the art use similar common approaches for preparing an immunogen. These methods include the use, in the vaccine, of integral sequences HIV-1 proteins, as recombinant proteins, recombinant DNA, or inserts in recombinant virus vectors.

Results of several vaccine trials that passed the pre-clinical stage were reported between 2003 and 2004. The Phase III trial (efficacy) of the REMUNE vaccine (combination of depleted whole inactive HIV-1 of the envelope protein), tested on over 5,000 individuals at risk of infection, failed to demonstrate protection and the trials were ended (McCarthy M, *HIV Vaccine fails vaccine trial,* THE LANCET, 361:755-756, 2003). In 2004, a promising candidate vaccine developed by a team from University of Oxford and University of Kenya reached the stage of Phase I/II trials but demonstrated immunogenicity in no more than one-third of tested individuals (International Conference Aids Vaccine 2004, Lausanne, Switzerland).

One of the disadvantages of the DNA vaccines, whether recombinant or from viral vectors encoding genes or whole proteins of the HIV-1, such as those already known in the state of the art, is the principle used by them, which facilitates the development of molecular escape mechanisms by the HIV-1 in response to immune and other pressures. Such a disadvantage may be one of the reasons for the failure of such vaccines. Furthermore, variation in the sequence may lead to several immunological escape mechanisms, while the immunization with T-cell epitopes from multiple viral gene products out of the context of native HIV-1 proteins can avoid recognition escape mechanisms, maintaining the induction of significative cellular immune responses (Newman M J et al, 2002).

In the specific and direct area of the development of a product, De Groot A S et al in *Engineering immunogenic consensus T helper epitopes for a cross-clade HIV vaccine* (2004) and in *HIV vaccine development by computer assisted design: the GAIA vaccine* (2005) identified conserved epitopes of the recognized HIV-1, over a large proportion of patients, by using computer-aided algorithms. The documents mentioned above also reported the insertion of said epitopes in vaccines undergoing testing at the pre-clinical stage with experimental animals. Previous reports also showed the selection of epitopes based on their ability to bind to multiple HLA molecules, with inferior results to those of De Groot A S et al, since HIV-1+ patients did not recognize said epitopes (Van den Burg S H et al, Journal of Immunology (1999), *Identification of a conserved universal Th epitope in HIV-1*). Wilson CC et al (Journal of Virology 2001. *Identification and antigenicity of broadly cross-reactive* . . . ) also use another search algorithm for sequences binding multiple HLA class II molecules, identifying a group of peptides frequently recognized by mononuclear blood cells of HIV-1+ patients.

Thus the development and testing of new formulations and combinations of epitopes remains a top priority in health research worldwide.

Among the broadly recognized challenges in obtaining effective vaccines against infections by HIV-1 (McMichael A J & Hanke T, *Nature Medicine* (2003)), the following are cited:

a) the construction of a vaccine capable of inducing high levels of neutralizing antibodies;

b) the construction of a vaccine capable of generating cellular immune responses (from T-lymphocyte) of greater intensity;

c) initiating new Phase III trials sooner, with an eventual combination of vaccines.

Although anti-HIV-1 cytotoxic CD8+ T-lymphocytes effectively destroy the cells infected by the virus, their activity is fundamentally dependent on the presence of anti-HIV-1 CD4+ T-cells (Rosenberg et al, 1997; Kalams et al, 1998; Heeney et al, 2002). Therefore, the incorporation of appropriate HIV-1 epitopes recognized by the CD4+ T-cells may be essential to the success of an anti-HIV-1 vaccine candidate. However, there are only a few epitopes known for HIV-1 CD4+ T-lymphocytes, when compared to the CD8+ epitopes, which have been much more searched for.

Therefore, it is necessary to identify new epitopes of HIV-1 that are recognized by the CD4+ T-cells in the majority of individuals. These epitopes may be incorporated in an candidate vaccine based on epitopes that generate immune responses in a significant proportion of the population exposed to the virus. It is expected that this strategy, together with new strategies for the formulation of immunogens, may lead to a protective vaccine.

However, the identification of such peptides is difficult and very expensive when using the traditional methodology of overlapping peptides: hundreds or thousands of peptides synthesized step by step, with the difference of a few amino acid residues, have to be tested. Furthermore, said approach may not identify some of the epitopes in the regions between adjacent peptides, thus being cumbersome and not totally effective.

Recent literature reports have identified HIV-1 epitopes by using algorithms, as mentioned above. However, the test results have not demonstrated the expected recognition potential of the epitopes, i.e., recognized by the greatest majority of HIV-1+ patients.

BRIEF DESCRIPTION OF THE SEQUENCE LISTING

The present invention will be more clearly understood upon reading the following non-restrictive detailed description and the Sequence Listing.

The Sequence Listing contains the 3-letter code for amino acids, as defined in accordance with the IUPAC-IUBMB standards described in *Nucleic Acids Res.*, 13:3,021-3,030 (1985), and in *Biochemical J.* 219, (no. 2):345-373 (1984).

The Sequence Listing presented herein has the objective of defining the amino acid sequences of 16 epitopes specific to HIV-1, for the first time identified as being widely recognized by CD4+ cells of patients with HIV-1, which are an object of the present invention.

BRIEF DESCRIPTION OF THE DRAWINGS

FIG. 1 shows the pVAX-HIVBr18 plasmid containing mammalian codon-optimized nucleotide sequence artificial multiepitope gene, encoding the 16 described epitopes subcloned in pVAX 1 vector.

BRIEF DESCRIPTION OF THE INVENTION

Figure 2:
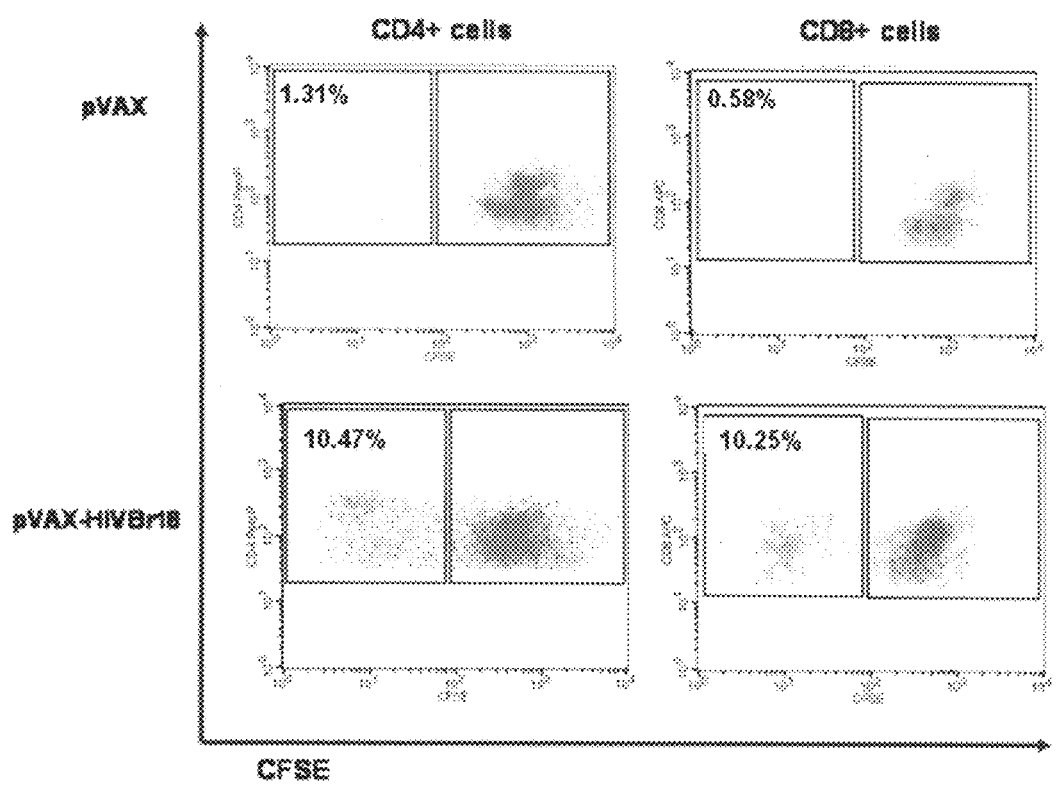
FIG. 2: Shows that CD4+ and CD8+ T cells from pVAX-HIVBr18 BALB/c immunized mice proliferate against the pooled HIV peptides encoded in pVAX-HIVBr18.
Figure 3A:
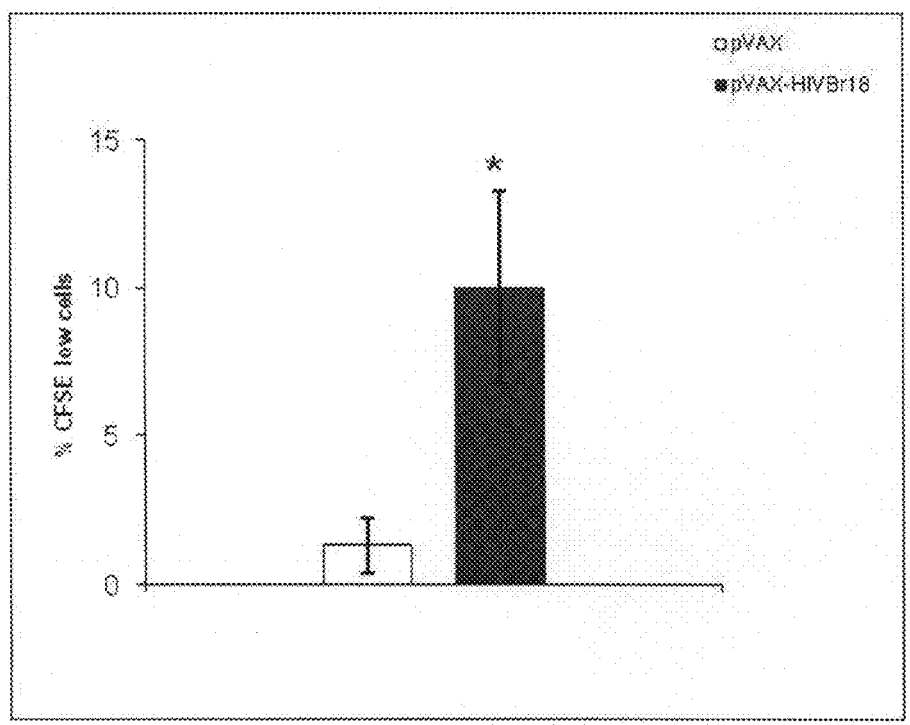
FIG. 3A and FIG. 3B show that CD4+ and CD8+ T cells from immunized mice are consistently able to proliferate against the pooled peptides (* indicates a significant difference when comparing the two groups ($p<0.01$)).
Figure 3B:
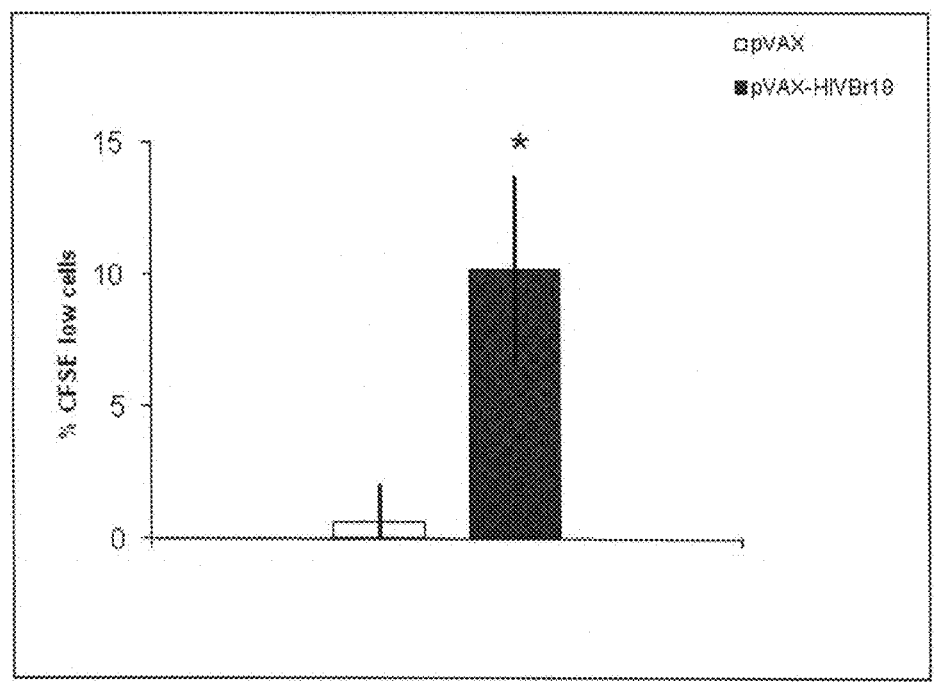
Figure 4:
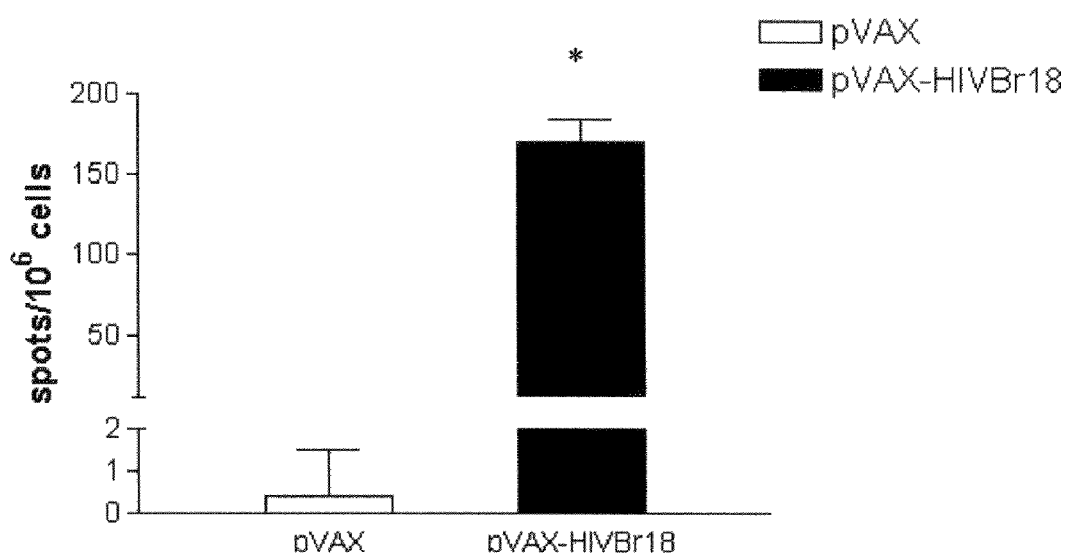
FIG. 4 shows IFN-γ ELISPOT assay against the pooled peptides; 6 individual experiments involving 60 BALB/c mice (* indicates a significant difference when comparing the two groups ($p<0.0001$).
Figure 5:
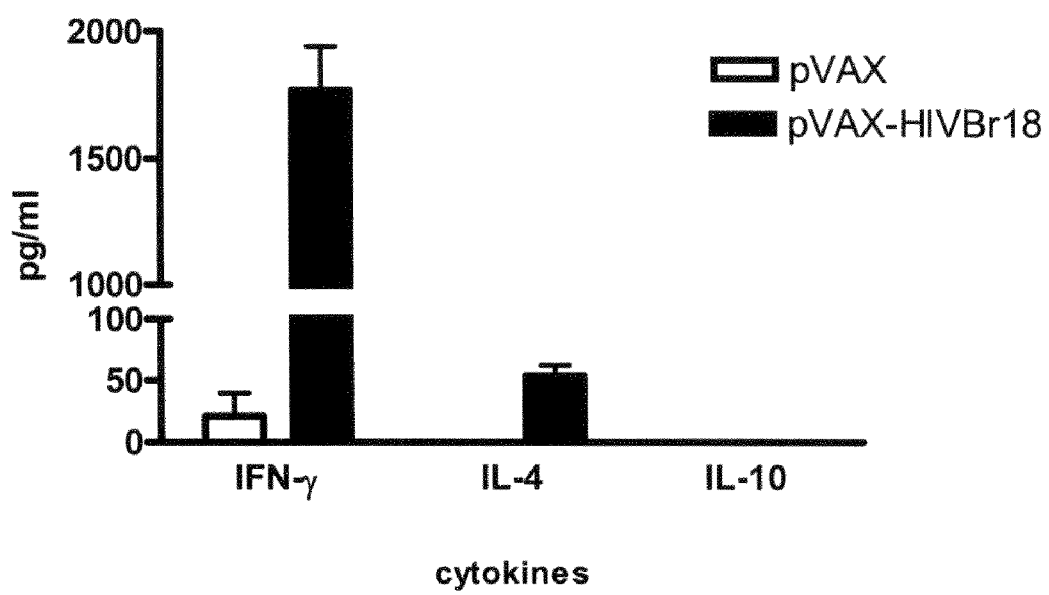
FIG. 5 shows cytokine detection in 5-day culture supernatants from splenocytes stimulated with the pooled HIV-1 peptides contained in pVAX-HIVBr18.
Figure 6:
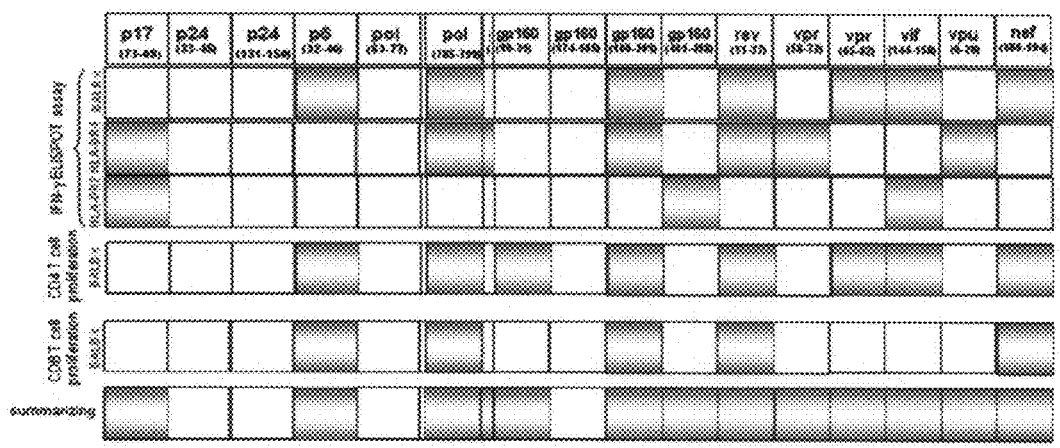
FIG. 6 shows a summary of responses of BALB/c and HLA class II transgenic mice to immunization with pVAX-HIVBr18.

The present invention refers to conserved and new, previously unknown, multiple epitopes of the HIV-1, which are widely recognized by CD4+ T-lymphocytes.

The present invention also refers to the use of said epitopes.

Other embodiments of the present invention are combinations comprising 2 or more of the new epitopes and the use of said combinations.

In addition, the present invention refers to compositions comprising at least one of the new epitopes and the use of said compositions.

Further objects of the present invention are prophylactic anti-HIV-1 vaccines and therapeutic vaccines, which contain one or more of said epitopes.

Moreover, the present invention refers to a method for the identification of new epitopes, which comprises the steps of:
 a) selection of sequences conserved from the consensus sequence of HIV-1 of subtype B, having at least 15 amino acid residues.
 b) selection, among the sequences selected in step a), of those that bind promiscuously multiple HLA-DR molecules;
 c) expansion of the sequences of said peptides selected at the N-terminal and C-terminal ends;
 d) confirmation of recognition of the selected peptides by T-lymphocytes of HIV-1+ patients.

Another embodiment of the present invention is a method for treating or preventing infections caused by the HIV-1 virus.

DETAILED DESCRIPTION OF THE INVENTION

The present invention refers to one or more synthetic peptides, either simple or having covalent modifications, such as miristoylation and other forms of lipopeptides, referred to herein as epitopes, conserved and isolated from the HIV-1 genome, which bind in a promiscuous manner multiple HLA-DR molecules and are recognized by CD4+ T-lymphocytes in patients infected by the HIV-1.

Said epitopes are selected from the group consisting of:

| | |
|---|---|
| EELRSLYNTVATLYCVH; | (SEQ ID NO.: 1) |
| SPEVIPMFSALSE; | (SEQ ID NO.: 2) |
| KRWIILGLNKIVRMYSPTSI; | (SEQ ID NO.: 3) |
| DKELYPLASLRSLFG; | (SEQ ID NO.: 4) |
| QRPLVTIKIGGQLKE; | (SEQ ID NO.: 5) |
| GKIILVAVHVASGYI; | (SEQ ID NO.: 6) |
| TMLLGMLMICSAA; | (SEQ ID NO.: 7) |
| ALFYKLDVVPID; | (SEQ ID NO.: 8) |
| NTSYRLISCNTSVI; | (SEQ ID NO.: 9) |
| SELYLYKVVKIEPLGVAP; | (SEQ ID NO.: 10) |
| ELLKTVRLIKFLYQSNP; | (SEQ ID NO.: 11) |
| EAIIRILQQLLFIHF; | (SEQ ID NO.: 12) |
| QQLLFIHFRIGCRHSRIG; | (SEQ ID NO.: 13) |
| SLQYLALVALVAPKK; | (SEQ ID NO.: 14) |
| VLEWRFDSRLAFHHV; | (SEQ ID NO.: 15) |
| VLAIVALVVATIIAI. | (SEQ ID NO.: 16) |

The corresponding sequence listing is mentioned at the end of each epitope.

Particularly, the epitopes of the present invention are selected from the group consisting of: EELRSLYNTVATLYCVH (SEQ ID NO.: 1), KRWIILGLNKIVRMYSPTSI (SEQ ID NO.: 3), QRPLVTIKIGGQLKE (SEQ ID NO.: 5), TMLLGMLMICSAA (SEQ ID NO.: 7), ALFYKLDVVPID (SEQ ID NO.: 8), ELLKTVRLIKFLYQSNP (SEQ ID NO.: 11) e VLAIVALVVATIIAI (SEQ ID NO.: 16).

The epitopes of the present invention are particularly derived from the gag, pol, env, rev, vpr, vif, nef and vpu proteins of HIV-1.

Said epitopes may be derived from any type of HIV-1 subtype but, preferably, they are derived from subtype B.

One of the advantages of the present invention is the recognition of said epitopes by CD4+ T-cells of multiple HIV-1 patients.

According to the present invention, "epitopes" mean the epitopes mentioned above, their functional equivalents and mimetic sequences thereof.

A "functional equivalent" refers to structurally distinct sequences, fragments, analogues, derivatives or associations, which perform the same function to achieve equal results. It is understood that any alterations made by those skilled in the art, which lead in an obvious manner to equivalent effects, shall also be considered as a part of the invention. More particularly, functional equivalents are the sequences presenting homology of at least 12 amino acids to the epitopes described above and perform the same function of said epitopes, exhibiting equal or similar results.

In accordance with the present invention, "mimetic sequences" are understood as being non natural amino acid sequences with modified structures, so that they present functions and results equal or similar to the sequences of the epitopes of the present invention.

The present invention also refers to the use of said epitopes.

One of the uses is in the preparation of a composition for treating disorders caused by the HIV-1 virus. Preferentially, said disorders are related to the immunologic system having been impaired, such as, for example, progressive destruction of lymphocytes.

Another use is as an additive in the preparation of anti-HIV-1 vaccine compositions already known in the state of the art, to provide T cell help and increase of the immunogenicity and protective properties thereof.

The epitopes of the present invention have further use in diagnostic methods and in trials for the evaluation of the immune response of CD4+ T-lymphocytes in patients with HIV-1.

The cellular immune response to the epitopes of HIV-1 shows correlation with progression of the disease. Therefore, the evaluation of immune responses against the epitopes of the present invention, in patients HIV-1+ patients during the infection, or in response to immunological interventions, is essential for studying the effectiveness of the vaccine or other intervention. Individually, the epitopes of the present invention have been recognized by between 18% and 44% of patients and not a single HIV-1 seronegative control individual. The group of 16 epitopes of the present invention was recognized by 32 of the 34 HIV-1+ patients tested (94%). Furthermore, patients with advanced disease and immunodeficiency showed reduced responses when compared to long-term nonprogressor (LTNP) HIV-1+ patients, demonstrating the efficacy for the evaluation of the HIV-1 specific immune response.

Furthermore, the epitopes of the present invention are useful for the preparation of anti-HIV-1 prophylactic vaccines or therapeutic vaccines. Said vaccines may be more effective than those already known in the state of the art since the new epitopes of the present invention are recognized by the T-cells in a majority of individuals, thus covering a significant proportion of the population exposed to the virus.

Another object of the present invention is a combination comprising two or more of the new epitopes and the uses of said combinations.

The uses of the combination are in accordance with the above descriptions, namely: in the preparation of a composition for treating disorders caused by the HIV-1 virus, as an additive in the preparation of anti-HIV-1 vaccine compositions already known in the state of the art, in diagnostic methods and tests for evaluating the immune response of CD4 T-lymphocytes of patients with HIV-1 and in the preparation of anti-HIV-1 prophylactic vaccines or therapeutic vaccines.

It is also en object of the present invention a composition comprising at least one of the new epitopes. Said composition further comprises a pharmaceutically acceptable carrier or vehicle.

The compositions of the present invention may be in the solid or liquid form. Said compositions may be formulated for a rapid or prolonged release of their components and may further comprise compounds for stimulating and/or inhibiting the immunologic system. Said compositions may be prepared in accordance with conventional methods already known in the state of the art.

Further objects of the present invention are uses of the composition described above. This includes the use of said composition in the preparation of anti-HIV-1 prophylactic vaccines or therapeutic vaccines, as an additive in the preparation of compositions of existing experimental anti-HIV-1 prophylactic vaccines, in diagnostic methods and tests for evaluating the immune response of CD4+ T-lymphocytes of patients with HIV-1, as described above for the new epitopes.

The present invention also refers to an anti-HIV-1 prophylactic vaccine or a therapeutic vaccine. Said vaccines comprise at least one of the epitopes described above, in association with one or more pharmaceutically acceptable adjuvants, vehicles, excipients, binding agents, carriers or preservatives.

Optionally, the vaccines of the present invention comprise a combination of epitopes or the composition of the present invention with one or more pharmaceutically acceptable adjuvants, vehicles, excipients, bonding agents, carriers or preservatives.

The vaccines in accordance with the present invention may be formulated according to the following forms, including one or more of the new epitopes:

a) combined with adjuvants or carriers as micro/nanoparticles/spheres;
b) a recombinant DNA construction with the sequences of one or more of the new epitopes, particularly containing other protein products, optionally inserted in carriers such as micro/nanoparticles/spheres;
c) a recombinant protein construction with sequences of the new epitopes, particularly combined with adjuvants, optionally inserted in carriers such as micro/nanoparticles/spheres;
d) a viral vector containing sequences of the new epitopes; and
e) a combination of the new epitopes with HIV-1 immunogens already known in the state of the art.

Another object of the present invention is a method for the identification of the new epitopes, which comprises the steps of:

a) selection of the peptides conserved from the consensus sequence of HIV-1 of subtype B, with at least 15 amino acids;
b) selection, among the peptides selected in step a), of those binding promiscuously multiple HLA-DR molecules;
c) expansion of the sequences of said peptides selected at the N-terminal and C-terminal ends;
d) confirmation of recognition of the selected peptides by T-lymphocytes of HIV-1+ patients.

An algorithm is used to screen the whole HIV-1 genome and to select sequences of HIV-1 proteins, which may bind multiple HLA-DR molecules commonly found in the population. Preferentially, the selection of step b) is carried out by means of a TEPITOPE algorithm (*Generation of tissue-specific and promiscuous HLA ligand databases using DNA chips and virtual HLA class II matrices*, Sturniolo, T et al, Nature Biotechnology 17, 555-562, 1999), which employs a matrix based on the results of real peptide binding tests for each one of the several HLA-DR molecules, and attributes scores to each sequence derived from the protein, selecting those having scores superior to the chosen threshold. In the case of the present invention, said selected peptides bind in a "promiscuous" manner to at least 18 HLA-DR molecules available on said algorithm, with a threshold of 3%.

After step b), 2 or 3 flanking residues are added to the N-terminal and C-terminal ends, in order to increase the frequency of peptide recognition.

Step d) is achieved by synthesizing the peptides representing the epitopes of the present invention, followed by ELISPOT assay to detect IFN-γ-producing cells. For the purposes of the present invention, the positivity cutoff value used is ≧30 SFC IFN-γ/10⁶ PBMC, calculated based on the levels of responses of HIV-1 seronegative patients Further aims of the present invention are methods for treating or preventing an infection caused by the HIV-1 virus. HIV-1 infection is related to the impairment of the immunologic system of the patient.

In accordance with the present invention, the method for treating or preventing comprises administering a therapeutically effective amount of the composition described herein to the patient. Optionally, said method comprises administering a therapeutically effective amount of the combination of epitopes of the present invention or anti-HIV-1 prophylactic vaccines or therapeutic vaccines described herein to the patient.

A "therapeutically effective amount" designates an amount of epitopes, a combination thereof, a composition or vaccine effective for the "treatment" of a disease or a disorder in a patient. As defined in the present invention, this is considered to be an amount capable of avoiding contagion, reducing the number of HIV-1 RNA copies/mm3 in the plasma, or increasing the number of CD4+ T-cells/mm3 in the peripheral blood of patients, or reducing the number of cells infected by the HIV-1 virus and/or improving one or more of the symptoms associated to the infections caused by the HIV-1 virus, as a result of inducing immune responses of the T-lymphocytes through the stimulation of the CD4+ T-cells by means of epitopes recognized by them.

According to the present invention, the administration to the patient can be made in any form, such as, for example, oral, intranasal, mucosal, local, transdermal and parenteral, (such as intravenous, intraperitoneal, intradermal, subcutaneous or intramuscular). Administration may also occur by means of the use of needle-less administration devices. Administration may further occur through the use of a combination of methods, such as being firstly administered parenterally with subsequent mucosal administration.

Preferably, administration is subcutaneous or intramuscular.

The following examples are illustrative and provide a clearer and more consistent understanding of the invention but are not intended to limit its scope.

EXAMPLES

Example 1

Identification of New Immunodominant Epitopes

To select the epitopes, sections of at least 15 consecutive conserved amino acids present in the consensus sequence (complete HIV-1 genome) of the HIV-1 subtype B (December 2002 version), available at the website: http://HIV-1-wev.lan-1.gov/content/index, were analyzed by using the TEPITOPE algorithm for the prediction of binding to HLA-DR molecules. The selected epitopes were those predicted to bind over the chosen threshold (3%) to the greatest possible number of HLA-DR molecules in a "promiscuous" manner. From the whole consensus viral genome of subtype B, epitopes of the proteins gag, env, pol, vpu, vpr, vif, vpu were selected capable of binding at least 18 of the 25 HLA-DR molecules available in the algorithm with a threshold of 3%, thus selecting epitopes with a high chance of binding HLA-DR molecules with great avidity. For each selected sequence (9-residue HLA-binding core), N- and C-terminal flanking residues were added, flanking so as to increase the percentage of patients recognizing each peptide.

Example 2

Evaluation of the Epitopes

In order to evaluate the capacity of the selected epitopes to be recognized by T-lymphocytes of HIV-1+ patients, said epitopes (described in Table 1 below) were synthesized in solid phase by using Fmoc chemistry and having a C-terminal amide.

TABLE 1

Sequences of the synthetic peptides encoding Potentially Promiscuous Epitopes Derived from conserved regions of clade B HIV-1 Consensus Sequence Selected by the TEPITOPE

| Identification | Peptides | Sequences | % of binding HLA molecules using TEPITOPE algorithm (3% threshold) |
|---|---|---|---|
| gag 1 | Gag (73-89)[1] | EELRSLYNTVATLYCVH[2] (SEQ ID NO: 1) | 72 |
| gag 2 | Gag (165-177) | SPEVIPMFSALSE (SEQ ID NO: 2) | 88 |
| gag 3 | Gag (263-282) | KRWIILGLNKIVRMYSPTSI (SEQ ID NO: 3) | 100 |
| gag 4 | Gag (480-494) | DKELYPLASLRSLFG (SEQ ID NO: 4) | 76 |
| pol 1 | Pol (63-77) | QRPLVTIKIGGQLKE (SEQ ID NO: 5) | 64 |
| pol 3 | Pol (694-708) | GKIILVAVHVASGYI (SEQ ID NO: 6) | 72 |

TABLE 1-continued

Sequences of the synthetic peptides encoding Potentially Promiscuous Epitopes Derived from conserved regions of clade B HIV-1 Consensus Sequence Selected by the TEPITOPE

| Identification | Peptides | Sequences | % of binding HLA molecules using TEPITOPE algorithm (3% threshold) |
|---|---|---|---|
| env 2 | Env (19-31) | TMLLGMLMICSAA (SEQ ID NO: 7) | 80 |
| env 3 | Env (178-189) | ALFYKLDVVPID (SEQ ID NO: 8) | 72 |
| env 4 | Env (198-211) | NTSYRLISCNTSVI (SEQ ID NO: 9) | 88 |
| env 5 | Env (487-504) | SELYLYKVVKIEPLGVAP (SEQ ID NO: 10) | 100 |
| rev 1 | rev (11-27) | ELLKTVRLIKFLYQSNP (SEQ ID NO: 11) | 88 |
| vpr 2 | vpr (58-72) | EAIIRILQQLLFIHF (SEQ ID NO: 12) | 96 |
| vpr 3 | vpr (65-82) | QQLLFIHFRIGCRHSRIG (SEQ ID NO: 13) | 72 |
| vif 2 | vif (144-158) | SLQYLALVALVAPKK (SEQ ID NO: 14) | 72 |
| nef 1 | nef (180-194) | VLEWRFDSRLAFHHV (SEQ ID NO: 15) | 52 |
| vpu 1 | vpu (6-20) | VLAIVALVVATIIAI (SEQ ID NO: 16) | 100 |

[1]Position of the amino acid region selected from the HIV-1 protein: gag (73-89): HIV-1 gag protein, sequence 73-89.
[2]Amino acid sequence of each selected peptide.

Synthetic peptide stocks were diluted to 25 mg/mL in dimethylsulphoxide, followed by ELISPOT assays for detection of IFN-γ-producing cells in response to the epitopes using peripheral blood mononuclear cells (PBMC) in 34 HIV-1+ patients of several clinical groups, long-term nonprogressors (LTNP), reconsituted, partial controllers, and progressors. Each epitope was tested in a concentration of 5 μM. The cryopreserved cells were maintained in culture for 16 hours, placed on plates in the presence of the epitopes, incubated for a further 18 hours, washed and ELISPOT plates were developed for the identification of spot-forming cells/Interferon-γ-producing cells (IFN-γ SFC), which were then counted in an automated counter (Zeiss KS ELISpot/Axioplan 2). Eight seronegative individuals were tested with all epitopes and all presented responses below 20 spots/$10^6$ PBMC; even the average plus 3 standard deviations was below 25 in all cases in the highest case (Table 2).

Table 2 below shows the frequency of the IFN-γ-producing cells in response to each of the HIV-1 peptides in 8 healthy control individuals, seronegative for HIV-1. The absence of response for any peptide, shown in all of the 8 individuals tested, demonstrates the specificity of the reaction for patients with HIV-1. Based on these results, 30 SFC/$10^6$ PBMC IFN-γ was established as positive definition point.

Table 3 below shows individual recognition responses for each peptide by the 34 HIV-1+ patients tested. The present invention is capable of identifying previously unknown multiple conserved epitopes of HIV-1, recognized by CD4+ T-lymphocytes.

Results

The present approach was capable of identifying previously unknown conserved multiple epitopes of HIV-1, recognized by CD4+ T-lymphocytes. The results herein indicate that 100% of the predicted epitopes were recognized by at least 6 of the 34 patients, and that 94% of the HIV-1+ patients tested recognized at least one of the 16 peptides tested. When compared to techniques well known in the state of the art, the results obtained by the present invention are superior, the epitopes of the present invention being more efficient. DeGroot et al (2004) used another algorithm to identify 10 HIV-1 consensus T cell epitopes, that were able to elicit IFN-γ Elispot responses in only 10 out of 34 (29%) HIV-1-infected LTNP patients. The increased frequency of peptide recognition observed in our study could be due the intrinsic immunogenicity of our selected peptides as compared to those of DeGroot et al. (2004) or to patient variability. Our results also differ from another study by De Groot et al. (2005), who identified 20 epitopes from HIV-1 consensus sequences. Fifteen out of 20 (75%) such peptides were recognized by less than 18% of their patients, while all peptides in our study were individually recognized by 18% or more of tested patients. Furthermore, we have shown that HIV-1-infected patients recognize on average 5 peptides. More than 75% recognized more than 2 peptides approximately 40% of them responded to 5 or more epitopes, and 6 patients (19%) responded to 10 or more epitopes, corroborating their antigenicity and immunodominance. The increased proportion of peptides recognized, together with the increased proportion of patients recognizing each peptide, indicates that the potential for recognition of multiple epitopes in the context of the present invention is visibly superior to those of working in similar concepts.

It can be noted that the patients recognized an average of 5.5 epitopes (minimum of one, maximum of 16). The peptide pol1 was recognized by 44% of the tested individuals, while the peptides gag3, rev1 and gag1 were recognized, individually, by 31% to 41% of the patients. The combination of 3 most frequently recognized peptides (pol1, gag3, rev1) was sufficient to elicit ELISPOT responses in 79% (27/34) of the tested HIV-1+ patients. It can also be noted that a combination of only 7 peptides (pol1, gag3, rev1, env3, env2, gag1, vpu1) elicited response from all 94% of patients displaying responses to at least one of the 16 peptides. Finally, it can be noted that the average response amplitude to the 16 peptides by each patient was of 722 IFN-$\gamma$/$10^6$-producing spots (minimum of 42, maximum of 4455). The data indicates that the tested peptides are frequently recognized by peripheral blood mononuclear cells in non-selected HIV-1+ patients, which indicates that they occur naturally during infection by HIV-1.

It should be noted that the sequences of the present invention are conserved in most major subtypes of HIV-1 studied (A,B,C,D,F). These observations reinforce the findings that our selected epitopes—or sequences highly homologous to them—are broadly represented across several clades of HIV-1, raising the possibility that patients infected with other non-clade B HIV-1 may also recognize epitopes originally identified in HIV-1 clade B consensus. Such sequences demonstrate the same immunodominant properties relating to other subtypes of HIV-1 and possess vaccine potential. The results obtained with the peptides of the present invention show that these peptides can be recognized by individuals with HIV-1 that do not carry the tested sequence, thus corroborating the concept of cross-reactivity and sustaining the possibility of crossclade immunization to afford protection against multiple subtypes of HIV-1 (Table 4).

TABLE 2

Frequency of T cells producing IFN-gamma in response to selected HIV-1 peptides among peripheral blood mononuclear cells from HIV-1 seronegative individuals

| | IFN-$\gamma$ spots/$10^6$ PBMC* | | | | | | | | | | |
|---|---|---|---|---|---|---|---|---|---|---|---|
| Peptides | C#01 | C#02 | C#03 | C#04 | C#05 | C#06 | C#07 | C#08 | Average (AV) | Standard deviation (SD) | AV + 3SD |
| Gag (73-89) | 0 | 7 | 0 | 2 | 0 | 0 | 0 | 5 | 1.7 | 2.8 | 10.0 |
| Gag (165-177) | 0 | 2 | 0 | 0 | 0 | 0 | 0 | 5 | 0.9 | 1.8 | 6.3 |
| Gag (263-282) | 0 | 12 | 5 | 12 | 0 | 0 | 0 | 0 | 3.6 | 5.4 | 20 |
| Gag (480-494) | 0 | 0 | 5 | 12 | 8 | 0 | 0 | 5 | 3.7 | 4.6 | 17.4 |
| Pol (63-77) | 0 | 0 | 20 | 12 | 3 | 0 | 1 | 5 | 5.1 | 7.3 | 26.9 |
| Pol (694-708) | 0 | 2 | 0 | 0 | 0 | 0 | 0 | 0 | 0.2 | 0.7 | 2.4 |
| Env(19-31) | 0 | 7 | 5 | 0 | 0 | 0 | 0 | 15 | 3.4 | 5.4 | 19.7 |
| Env(178-189) | 5 | 0 | 0 | 7 | 0 | 0 | 0 | 0 | 1.5 | 2.8 | 10 |
| Env(198-211) | 0 | 7 | 15 | 2 | 3 | 0 | 0 | 15 | 5.2 | 6.4 | 24.6 |
| Env(487-504) | 0 | 0 | 5 | 0 | 0 | 0 | 0 | 0 | 0.6 | 1.8 | 5.9 |
| rev(11-27) | 5 | 7 | 5 | 7 | 0 | 0 | 0 | 0 | 3 | 3.3 | 12.9 |
| vpr(58-72) | 0 | 12 | 15 | 0 | 0 | 0 | 0 | 10 | 4.6 | 6.5 | 24.2 |
| vpr(65-82) | 0 | 8 | 7 | 0 | 0 | 0 | 0 | 0 | 1.9 | 3.5 | 12.3 |
| vif(144-158) | 0 | 8 | 2 | 0 | 0 | 0 | 0 | 15 | 3.1 | 5.5 | 19.7 |
| vpu(6-20) | 0 | 0 | 7 | 7 | 0 | 0 | 6 | 10 | 3.7 | 4.2 | 16.2 |
| nef(180-194) | 0 | 3 | 7 | 12 | 8 | 0 | 0 | 5 | 4.4 | 4.4 | 17.7 |

SFC/$10^6$ PBMC were calculated according to the following equation: (average spots in duplicate peptide wells − average spots in duplicate control wells) * 5.
Positive responses ($\geq$30 SFC/$10^6$ PBMC).

TABLE 3

Recognition of the selected HIV-1 clade B conserved consensus epitopes, by peripheral blood mononuclear cells in patients chronically infected by HIV-1 in several phases of clinical progression, using the IFN-γ ELISPOT assay Number of IFN-γ/10⁶ PBMC

| Peptides | LTNP | | | | | | | | Reconstituted | | | | | | | Partial Controllers | | | | | | | | |
|---|---|---|---|---|---|---|---|---|---|---|---|---|---|---|---|---|---|---|---|---|---|---|---|---|
| | 01 | 03 | 10 | 12 | A6 | 09 | 16 | A2 | A33 | A29 | A10 | A22 | A20 | A25 | A13 | A24 | A42 | A19 | A21 | A18 | A11 | A27 | A36 | A37 |
| | | | | | | | | | 0 | | | | 4 | | 17 | | | | | | | | | |
| Gag (73-89) | 0 | ▓ | 0 | ▓ | ▓ | ▓ | 0 | 20 | ▓ | ▓ | ▓ | | ▓ | | | 15 | 0 | 19 | 0 | 0 | 0 | 0 | 0 | 5 |
| Gag (165-177) | ▓ | 0 | ▓ | 0 | 0 | ▓ | 0 | ▓ | ▓ | 0 | 0 | 7 | 0 | 19 | 2 | 5 | 0 | 9 | 3 | 20 | 0 | 12 | ▓ | 0 |
| Gag (263-282) | ▓ | 0 | ▓ | ▓ | 0 | ▓ | ▓ | ▓ | ▓ | 0 | ▓ | ▓ | 0 | 29 | 0 | 5 | 0 | 24 | 0 | ▓ | 0 | ▓ | 0 | 20 |
| Gag (480-494) | 23 | 7 | ▓ | ▓ | 0 | ▓ | 0 | 0 | 26 | 0 | 0 | ▓ | 0 | 9 | 12 | 10 | 0 | ▓ | 0 | ▓ | 15 | 0 | 0 | 5 |
| Pol (63-77) | 10 | 7 | ▓ | ▓ | ▓ | ▓ | 0 | 0 | 1 | 0 | 0 | ▓ | 19 | 0 | 7 | ▓ | 0 | ▓ | 8 | ▓ | 0 | ▓ | ▓ | ▓ |
| Pol (694-708) | 16 | ▓ | 25 | 0 | 0 | ▓ | ▓ | 5 | 11 | 0 | ▓ | ▓ | 0 | 9 | 17 | ▓ | 0 | 19 | 8 | 10 | 15 | 12 | 12 | ▓ |
| Env (19-31) | ▓ | 0 | ▓ | ▓ | 0 | ▓ | ▓ | 5 | 0 | 0 | 5 | 2 | ▓ | ▓ | 2 | 0 | 0 | 0 | 13 | ▓ | 0 | 0 | 7 | 0 |
| Env (178-189) | 17 | 10 | ▓ | 10 | 0 | ▓ | 0 | 10 | 0 | 25 | 5 | 0 | 19 | 0 | 2 | 0 | 3 | ▓ | 8 | 0 | ▓ | ▓ | ▓ | ▓ |
| Env (198-211) | 0 | 7 | 0 | ▓ | 0 | ▓ | 0 | 5 | 0 | 20 | 25 | 12 | 14 | 0 | 0 | 0 | 0 | 14 | ▓ | 15 | 0 | ▓ | ▓ | ▓ |
| Env (487-504) | 13 | ▓ | ▓ | ▓ | 0 | ▓ | 0 | 0 | 0 | 0 | 0 | 27 | 29 | 0 | 0 | 25 | 0 | ▓ | 0 | 5 | 15 | 22 | ▓ | 15 |
| rev (11-27) | 3 | ▓ | 0 | ▓ | 8 | ▓ | 0 | 0 | ▓ | ▓ | 0 | 17 | 0 | ▓ | 7 | 10 | 0 | ▓ | 0 | ▓ | 20 | ▓ | ▓ | 25 |
| vpr (58-72) | 3 | 0 | 0 | ▓ | 23 | ▓ | 0 | 20 | 0 | 0 | 5 | 0 | 24 | ▓ | 0 | 20 | 0 | ▓ | ▓ | 0 | ▓ | 0 | 0 | 20 |
| vpr (65-82) | ▓ | 27 | 0 | ▓ | 0 | ▓ | 15 | 5 | 0 | 0 | 5 | 17 | ▓ | 0 | 12 | ▓ | 0 | ▓ | 0 | ▓ | 10 | 0 | ▓ | ▓ |
| vif (144-158) | 0 | 10 | ▓ | ▓ | 0 | ▓ | 10 | 20 | 0 | 25 | 25 | ▓ | 0 | 0 | 2 | ▓ | 0 | ▓ | ▓ | 0 | 0 | 0 | ▓ | ▓ |
| vpu (6-20) | 3 | 27 | 0 | 25 | 0 | ▓ | 0 | 20 | 1 | ▓ | 10 | 7 | 19 | 24 | ▓ | 10 | 0 | 19 | 0 | ▓ | 0 | ▓ | ▓ | ▓ |
| nef (180-194) | ▓ | ▓ | 0 | ▓ | 0 | ▓ | 0 | 0 | 0 | 10 | 0 | 0 | 4 | 0 | 17 | ▓ | 0 | 9 | 0 | 0 | 0 | ▓ | ▓ | ▓ |
| Number of recognized Peptides | 5 | 5 | 8 | 12 | 2 | 16 | 3 | 2 | 4 | 2 | 3 | 6 | 2 | 4 | 1 | 5 | 0 | 8 | 3 | 7 | 2 | 7 | 10 | 8 |
| Sum of spots** | 454 | 1625 | 710 | 1345 | 166 | 3805 | 1920 | 855 | 144 | 90 | 965 | 337 | 73 | 1506 | 42 | 280 | 0 | 482 | 199 | 325 | 105 | 419 | 2195 | 570 |

Number of IFN-γ/10⁶ PBMC

| Peptides | Progressors | | | | | | | | n | %* |
|---|---|---|---|---|---|---|---|---|---|---|
| | 11 | 05 | 06 | 15 | A3 | A35 | A31 | A34 | | |
| | | | | | | | | 0 | | |
| Gag (73-89) | 20 | 5 | 2 | 0 | 0 | ▓ | | ▓ | 10 | 31.3 |
| Gag (165-177) | 0 | 0 | 0 | 17 | 0 | ▓ | 0 | ▓ | 8 | 25.0 |
| Gag (263-282) | ▓ | 0 | ▓ | 0 | 5 | 20 | 0 | 0 | 13 | 40.6 |
| Gag (480-494) | 0 | 0 | 0 | 0 | 0 | ▓ | 0 | ▓ | 8 | 25.0 |
| Pol (63-77) | 0 | ▓ | 17 | 0 | 25 | ▓ | 0 | ▓ | 14 | 43.8 |
| Pol (694-708) | 15 | 0 | 0 | 17 | 5 | 20 | 0 | ▓ | 8 | 25.0 |
| Env (19-31) | 15 | ▓ | 2 | 0 | 15 | 10 | 0 | ▓ | 10 | 31.3 |
| Env (178-189) | 0 | 0 | 0 | 0 | ▓ | 15 | 0 | ▓ | 9 | 28.1 |
| Env (198-211) | 0 | 0 | 7 | 0 | 20 | 15 | 0 | ▓ | 7 | 21.9 |
| Env (487-504) | 20 | 15 | 0 | 0 | 15 | 0 | 0 | ▓ | 7 | 21.9 |
| rev (11-27) | 25 | 0 | 12 | 2 | 25 | 0 | 0 | ▓ | 11 | 34.4 |
| vpr (58-72) | 20 | 5 | 0 | 7 | 5 | 0 | 0 | ▓ | 7 | 21.9 |
| vpr (65-82) | 15 | 0 | 7 | 0 | 15 | 25 | 0 | 7 | 9 | 28.1 |
| vif (144-158) | 15 | 0 | 12 | 0 | 20 | 20 | 0 | ▓ | 10 | 31.3 |
| vpu (6-20) | 5 | ▓ | 2 | 7 | 5 | ▓ | 0 | 0 | 9 | 28.1 |
| nef (180-194) | 10 | 10 | 0 | 0 | 0 | 0 | 0 | ▓ | 9 | 28.1 |
| Number of recognized Peptides | 1 | 3 | 1 | 0 | 1 | 5 | 0 | 13 | | |
| Sum of spots** | 30 | 200 | 107 | 0 | 35 | 445 | 0 | 1571 | | |

SFC/10⁶ PBMC were calculated according to the following equation: (average spots in duplicate peptide wells − average spots in duplicate control wells)

*5. Positive responses (≧30 SFC/10⁶ PBMC) are highlighted in gray background.

TABLE 4

Percentage of isolates of each HIV-1 subtype bearing sequences identical to the immunodominant epitopes of the HIV-1 clade B consensus.

| Identification | Peptides | A | B | C | D | F |
|---|---|---|---|---|---|---|
| Gag 1 | Gag (73-89)[1] | ▓ | 25 | ▓ | ▓ | 0 |
| Gag 2 | Gag (165-177) | ▓ | 92 | 0 | ▓ | ▓ |
| Gag 3 | Gag (263-282) | ▓ | 55 | 3(85) | 0(80) | 0(89) |
| Gag 4 | Gag (480-494) | 0 | 36 | 0 | 0 | 0 |
| Pol 1 | Pol (63-77) | 0 | 49 | 3 | ▓ | ▓ |
| Pol 3 | Pol (694-708) | ▓ | 51 | ▓ | 0(80) | ▓ |
| Env 2 | Env (19-31) | 0 | 18 | 0 | 11 | 0 |
| Env 3 | Env (178-189) | 0 | 18 | 0 | 6 | 0 |
| Env 4 | Env (198-211) | 0 | 12 | 0 | 0 | 0 |
| Env 5 | Env (487-504) | 0(71) | 0(47) | 0 | 0 | 0 |
| Rev 1 | rev (11-27) | 0 | 25 | 0 | 0 | 0 |
| Vpr 2 | vpr (58-72) | ▓ | 57 | ▓ | ▓ | ▓ |
| Vpr 3 | vpr (65-82) | 0 | 25 | 0 | 0 | 0 |
| Vif 2 | vif (144-158) | 0 | 1 | 0 | 0 | 0 |
| Nef 1 | nef (180-194) | 0 | 1 | 0 | 0 | 0 |
| Vpu 1 | vpu (6-20) | 0 | 5 | 0 | 0 | 0 |

Consensus sequences which are present in 20% or more of the isolates in clade B HIV-1 are underlined.
Shaded areas represent non-B clade sequences with significant representation of sequences identical to immunodominant consensus B subtype epitopes.
Numbers in parentheses represent the percentage of isolates with single amino acid divergences in relation to immunodominant consensus B subtype epitopes.

Example 3

Development and Assay of Immunogenicity of a Multiepitope DNA Vaccine Encoding the Combination of HIV-1 Epitopes With a view to assay the immunogenicity of a vaccine construct including the HIV-1 epitopes, a DNA vaccine was constructed, encoding the epitopes in tandem, with GPGPG spacers to reduce formation of junctional epitopes.

1. Multiepitope DNA Vaccine Design

A multiepitope DNA was constructed encoding the codon-optimized version of the HIV-1 epitopes (Fonseca et al., 2006) separated by a GPGPG spacer and subcloned in the pVAX1 vector (pVAX-HIVBr18). Animals were immunized three times intramuscularly 2 weeks apart with 100 μg of pVAX-HIVBr18 or pVAX1 alone. Antigen-specific immune responses against the 16 individual or pooled synthetic peptides were evaluated 15 days after the last immunization using CFSE dilution protocol for proliferation, the IFN-γ ELISPOT assay and ELISA-based cytokine detection in culture supernatants.

The pVAX-HIVBr18 plasmid containing mammalian codon-optimized nucleotide sequence artificial multiepitope gene, encoding the 16 described epitopes subcloned in pVAX 1 vector, is shown in FIG. 1.

2. Immunization with pVAX-HIVBr18 Induces Significant CD4 and CD8 T Cell Proliferation Three biweekly subcutaneous immunizations with 100 ug pVAX-1 or pVAX-HIV-1 were able to elicit proliferation of over 10% of $CD4^+$ and $CD8^+$ $CD3^+$ splenocytes in response to pooled peptides. Pooled splenocytes from immunized mice were stained with CFSE, incubated with pooled peptides for 5 days, immunostained with anti-CD3, CD4 and CD8 and analyzed by a flow cytometer in a CFSE dilution protocol. CD3+CD4+$CFSE^{low}$ and CD3+CD8+$CFSE^{low}$ cells were considered as having proliferated (FIG. 2).

FIG. 3 refers to a proliferation assay using CFSE dilution protocol, showing the average and standard deviation of 4 individual experiments involving 40 BALB/c mice. The CD4 T cells (A) and CD8+ T cells (B) from BALB/c mice immunized with pVAX-HIVBr18 but not pVAX were consistently able to proliferate against the pooled peptides. Mean±SD of 4 individual experiments.

3. Immunization with pVAX-HIVBr18 Elicited IFN-γ-Producing Splenocytes

An IFN-γ ELISPOT assay against the pooled peptides was carried out (6 individual experiments involving 60 BALB/c mice). Strong IFN-γ production was observed in splenocytes from pVAX-HIVBr18 BALB/c immunized mice (FIG. 4).

4. Immunization with pVAX-HIVBr18 elicited a Th1 response

The presence of IFN-γ, IL-4 and IL-10 cytokines in culture supernatants was evaluated after 5 days of culture stimulation with the pooled peptides. High IFN-γ production was observed, while there was little production of IL-4 and IL-10 was not detected in culture supernatants (FIG. 5).

5. Responses Elicited by Immunization of BALB/c Mice are Multiepitopic, Covering Epitopes from 8 Major HIV-1 Proteins Responses elicited in BALB/c mice by pVAX-HIVBr18 were multiepitopic, covering 9 out 16 epitopes included in the present application, that are represented in the multiepitopic DNA construction of the invention. It was observed that 8 peptides were able to induce CD4+ T cell proliferation while 5 peptides were able to induce CD8+ T cell proliferation. FIG. 6 shows that seven individual peptides were able to elicit IFN-γ production by splenocytes from BALB/c mice immunized with pVAX-HIVBr18. These responses are summarized in FIG. 6.

6. pVAX-HIVBr18 Induces Multiepitopic and Multiallelic Responses in HLA Class II Transgenic Mice The same immunization protocols were applied in I-$A_D$-HLA-DR2 and I-$A_0$-HLA-DR4 transgenic mice not expressing their endogenous MHC class II as a means to assess T cell responses of genetically heterogeneous human populations. HLA-DR-transgenic mice were immunized with pVAX-HIVBr18 and the antigen-specific immune responses were evaluated. FIG. 6 is a summary of the responses obtained to HLA class II transgenic and BALB/c mice. Peptides that elicit CD4+/CD8+ T cell proliferation and/or IFN-γ production are marked. These responses are multiallelic, covering different MHC class II molecules, an important feature to a vaccine candidate. It was also observed that the immune responses are multiepiepitopic, covering all of the epitopes from HIV accessory/regulatory proteins and include epitopes from all other HIV proteins included in the vaccine.

7. Conclusion

The results described above and illustrated in FIGS. 1 to 6 indicated that immunization with pVAX-HIVBr18 encoding the 16 frequently recognized conserved HIV epitopes elicits potent CD4+ and CD8+ T cell responses to multiple (12 out of the 16) HIV epitopes, possibly overcoming the immunodominance problem. This response was polyallelic since different epitope profiles were recognized in BALB/c and two different HLA class II transgenic mice and fully supports the immunogenicity claims that may lead to its eventual use in humans as an anti-HIV-1 vaccine.

The invention claimed is:

1. An anti-HIV immunogen comprising a recombinant DNA construct having a combination of at least 7 coding sequences of the epitopes of SEQ ID NO: 1 to SEQ ID NO: 16, wherein one of the coding sequences encodes SEQ ID NO: 10.

2. An anti-HIV immunogen comprising a viral vector containing a combination of at least 7 coding sequences of the epitopes of SEQ ID NO: 1 to SEQ ID NO: 16, wherein one of the coding sequences encodes SEQ ID NO: 10.

3. An anti-HIV immunogen comprising a recombinant DNA construct according to claim 1, wherein said combination comprises, besides a sequence encoding for SEQ ID NO: 10, the coding sequences of the epitopes SEQ ID NO: 1, SEQ ID NO: 3, SEQ ID NO: 5, SEQ ID NO: 7, SEQ ID NO: 8, SEQ ID NO: 11 and SEQ ID NO: 16.

4. An anti-HIV immunogen comprising a viral vector according to claim 2, wherein said combination comprises, besides a sequence encoding for SEQ ID NO:10, the coding sequences of the epitopes SEQ ID NO: 1, SEQ ID NO: 3, SEQ ID NO: 5, SEQ ID NO: 7, SEQ ID NO: 8, SEQ ID NO: 11 and SEQ ID NO: 16.

5. An anti-HIV immunogen comprising a recombinant DNA construction according to claim 1, wherein said combination of at least 7 coding sequences of the epitopes comprises every sequence from SEQ ID NO.: 1 to SEQ ID NO.: 16.

6. An anti-HIV immunogen comprising a viral vector according to claim 2, wherein said combination of at least 7 coding sequences of the epitopes comprises every sequence from SEQ ID NO.: 1 to SEQ ID NO.: 16.

7. An anti-HIV immunogen according to any one of claims 1, 2 and 3-5, further comprising one or more of pharmaceutically acceptable adjuvants, excipients, binding agents, carriers or preservatives.

8. An anti-HIV immunogen comprising a recombinant DNA construct having a combination of every sequence from coding sequences of the epitopes of SEQ ID NO: 1 to SEQ ID NO: 16.

9. An anti-HIV immunogen comprising a viral vector containing a combination of every sequence from coding sequences of the epitopes of SEQ ID NO: 1 to SEQ ID NO: 16.

10. An anti-HIV immunogen according to any one of claims 8 and 9, further comprising one or more of pharmaceutically acceptable adjuvants, excipients, binding agents, carriers or preservatives.

11. A method of inducing an immune response comprising administering the anti-HIV immunogen of claim 1.

12. A method of inducing an immune response comprising administering the anti-HIV immunogen of claim 2.

13. A method of inducing an immune response comprising administering the anti-HIV immunogen of claim 8.

14. A method of inducing an immune response comprising administering the anti-HIV immunogen of claim 9.

* * * * *